United States Patent [19]

Bokros

[11] 4,254,508
[45] Mar. 10, 1981

[54] BILEAFLET HEART VALVE WITH IMPROVED PIVOT

[75] Inventor: Jack C. Bokros, Alpine, Calif.

[73] Assignee: Carbomedics, Inc., San Diego, Calif.

[21] Appl. No.: 61,660

[22] Filed: Jul. 30, 1979

Related U.S. Application Data

[63] Continuation-in-part of Ser. No. 894,166, Apr. 6, 1978, Pat. No. 4,178,639.

[51] Int. Cl.³ .............................................. A61F 1/22
[52] U.S. Cl. ...................................... 3/1.5; 137/512.1; 137/527.8
[58] Field of Search ................ 3/1.5, 1; 137/512.1, 137/527, 527.8

[56] References Cited

U.S. PATENT DOCUMENTS

| | | | |
|---|---|---|---|
| 3,370,305 | 2/1968 | Gott et al. | 3/1.5 |
| 3,448,465 | 6/1969 | Pierce et al. | 3/1.5 |
| 3,579,645 | 5/1971 | Bokros | 3/1.5 |
| 3,835,475 | 9/1974 | Child | 3/1.5 |
| 3,903,548 | 9/1975 | Nakib | 3/1.5 |
| 4,078,268 | 3/1978 | Possis | 3/1.5 |
| 4,114,202 | 9/1978 | Roy et al. | 3/1.5 |
| 4,159,543 | 7/1979 | Carpentier | 3/1.5 |

FOREIGN PATENT DOCUMENTS

| | | | |
|---|---|---|---|
| 2846299 | 5/1979 | Fed. Rep. of Germany | 3/1.5 |
| 1160008 | 7/1969 | United Kingdom | 3/1.5 |

*Primary Examiner*—Ronald L. Frinks
*Attorney, Agent, or Firm*—Fitch, Even, Tabin, Flannery & Welsh

[57] ABSTRACT

A Bileaflet Heart Valve where two leaflets open and close a cylindrical passageway through an annular body. An improved pivot for the leaflets uses a pair of generally triangular depressions in opposed supports that extend above the body. Each depression includes a curved edge bridging two straight edges that converge to a curved vertex. Elongated guides extend from opposite ends of each leaflet and define the pivotal axis. Each guide pivots on its rounded end in the region of the curved vertex as the leaflets open and close the passageway.

8 Claims, 13 Drawing Figures

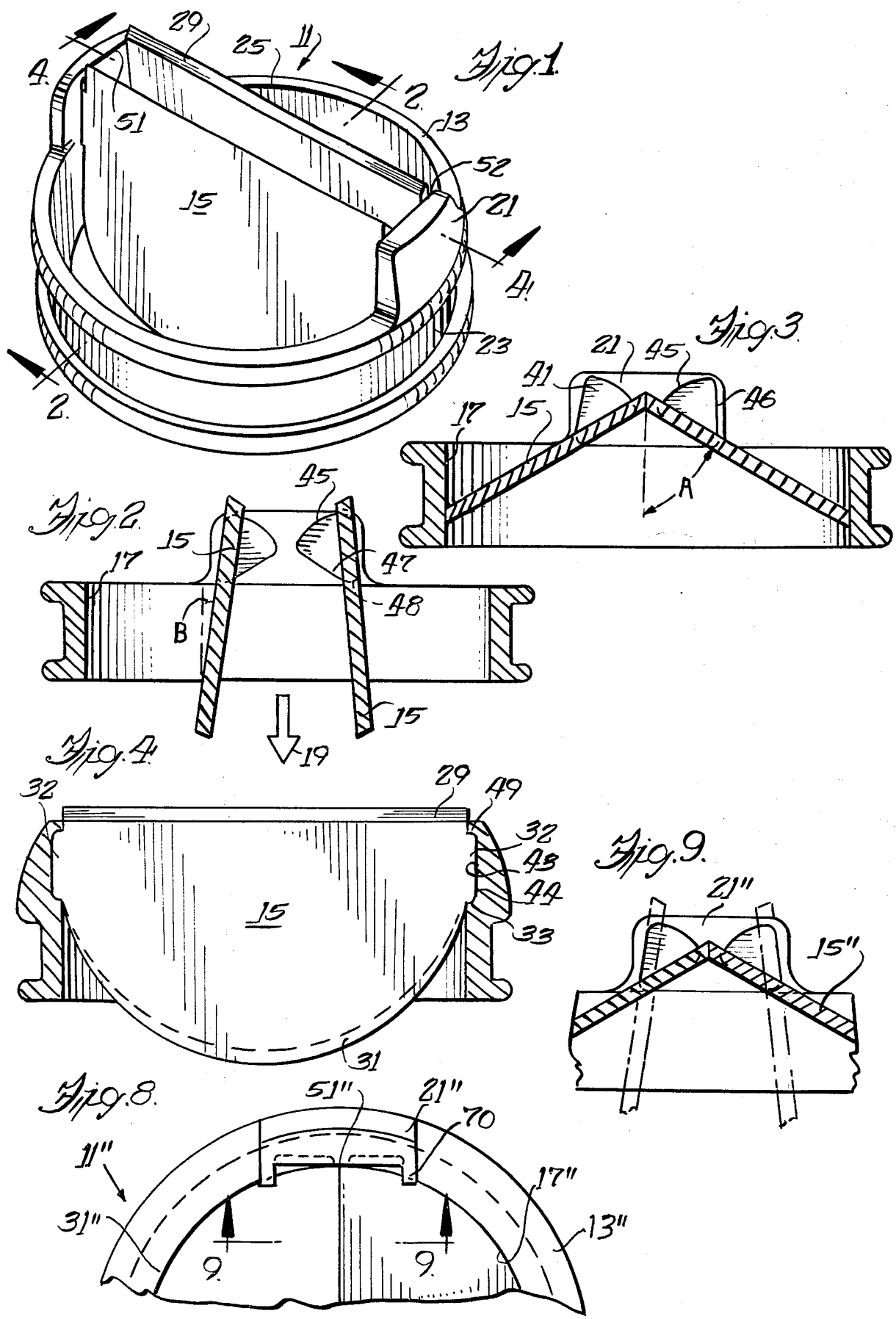

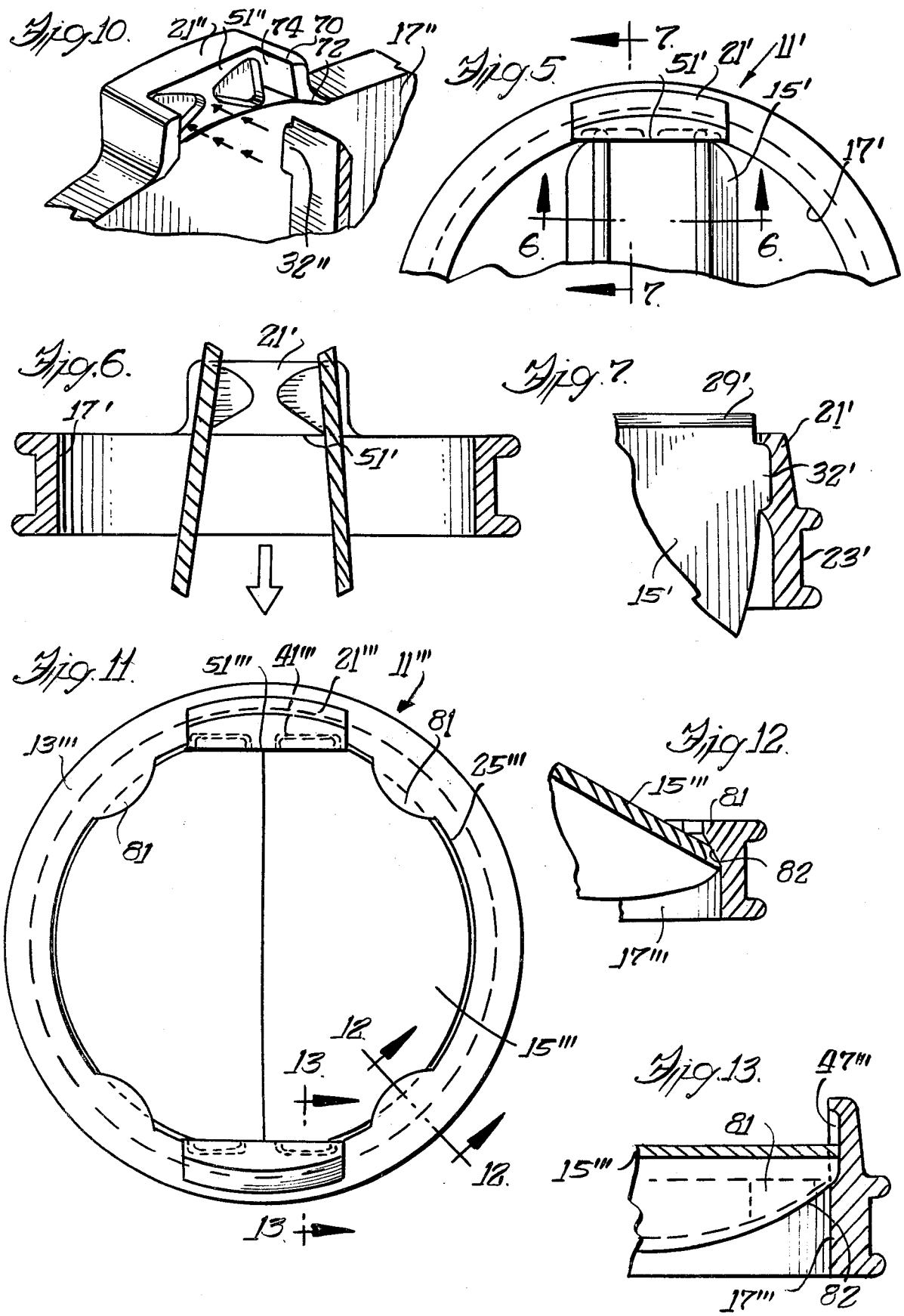

BILEAFLET HEART VALVE WITH IMPROVED PIVOT

This application is a continuation-in-part of my application Ser. No. 894,166, filed Apr. 6, 1978, entitled "Two-Leaflet Heart Valve" which issued as U.S. Pat. No. 4,178,639.

BACKGROUND OF THE INVENTION

This invention is related to heart valve prostheses for replacement of defective natural valves and more particularly to heart valve prostheses using pivotal valve members.

Various types of heart valve prostheses have been developed which operate hemodynamically as a result of the pumping action of the heart. Some of these valves which have been used employ a ball-and-cage arrangement, whereas others have used a disc-type arrangement for the valve member. Exemplary of a disc of the free floating type is U.S. Pat. No. 3,534,411, issued Oct. 20, 1970. Various disc-type valves having a pivotal arrangement have been developed, such as that shown in U.S. Pat. No. 3,546,711 to Bokros, issued Dec. 15, 1970, and that shown in U.S. Pat. No. 3,859,668, issued Jan. 14, 1975.

Disc-type heart valves have also been developed which use two members or leaflets, instead of a single disc, which leaflets rotate about parallel axes as a part of the opening and closing of the valve. It is the latter type of heart valve prostheses to which the present invention is directed.

SUMMARY OF THE INVENTION

The invention provides an improved version of a leaf type heart valve prosthesis. A pair of elongated guides extend from each of the leaflets which are received in mating depressions formed in a pair of supports extending upward from the annular valve body. The mating depressions are generally triangular in shape with a curved vertex that serves as a pivot for the rounded lower end of the elongated guide. The straight side edges of the triangle may limit the pivoting movement of each leaflet between its open and closed position. The heart valve opens and closes easily and reliably and exhibits excellent resistance to wear because of its design.

IN THE DRAWINGS

FIG. 1 is a perspective view of a heart valve embodying various features of the invention and having a pair of leaflet members which are shown in the open position;

FIG. 2 is a sectional view taken generally along the line 2—2 of FIG. 1;

FIG. 3 is a sectional view similar to FIG. 2 but showing the leaflets in a closed position;

FIG. 4 is a sectional view taken generally along the line 4—4 of FIG. 1;

FIG. 5 is a top view of an alternative embodiment of this invention in which support means overhang the valve passageway;

FIG. 6 is a sectional view taken generally along the line 6—6 of FIG. 5;

FIG. 7 is a fragmentary section view generally along line 7—7 of FIG. 5;

FIG. 8 shows a fragmentary top view of another embodiment of a valve in which the supports also provide stop means for the open and closed valve positions;

FIG. 9 shows a fragmentary section view taken generally along line 9—9 of FIG. 8;

FIG. 10 is a fragmentary view of the valve shown in FIG. 8 with lines drawn to illustrate how guides on the leaflets mate with depressions in the supports;

FIG. 11 is a top view of still another alternative embodiment of a valve in which closed position stops are provided on the interior wall of the valve passageway;

FIG. 12 is a fragmentary section view taken generally along line 12—12 of FIG. 11; and FIG. 13 is a fragmentary section view taken generally along line 13—13 of FIG. 11.

DETAILED DESCRIPTION OF THE PREFERRED EMBODIMENTS

Illustrated in FIG. 1 is a heart valve 11 which has an annular valve body or housing 13 which carries a pair of pivoting leaflets or valve members 15 which open and close to control the flow of blood through a central passageway 17 in the direction of the arrow 19 (FIG. 2). The leaflets 15 are supported about eccentric axes by a pair of diametrically opposed supports 21 which extend upwardly from the annular valve body 13 as depicted in FIG. 1. It should of course be understood that the valve 11 can operate in any orientation and is not significantly affected by gravity; however, for ease of explanation, the valve 11 is shown and described with the supports 21 upstanding from the annular valve body 13.

The valve body is formed with a peripheral groove 23 about its exterior surface that accommodates a suturing ring (not shown) which may be any of the various types already well-known in the art. The suturing ring, of course, facilitates the sewing or suturing of the heart valve 11 to the heart tissue.

The passageway 17 through the valve body 13 is preferably circular and, accordingly, the internal wall surface 25 of the valve body which defines the passageway 17 preferably has the shape of a right circular cylinder.

The valve body 13 and the leaflets 15 may be made of any suitable material that is biocompatible and non-thrombogenic and that will take the wear to which it will be subjected during countless openings and closings of the leaflets. Preferably, the components are made from isotropic graphite, such as that sold under the tradename POCO, which has been suitably coated with pyrolytic carbon, such as that sold under the trademark PYROLITE, which gives excellent compatibility and wear-resistance.

The illustrated leaflets 15 are flat and have a uniform thickness throughout, as best seen in FIG. 2. A minor edge 29 of the leaflet 15 is straight, and the major edge 31 is curved in a manner to match the inner surface of the passageway 17. Accordingly, the outline of the arcuate major edge 31 is generally defined by a plane cutting the right cylindrical interior wall surface 25 of the valve body 13. The minor 29 and major 31 edges of the leaflets 15 are appropriately beveled so that in the closed position of the valve 11 the major edge 31 fits against the interior wall 25 while the minor edge 29 of each of the two leaflets fits together.

The pivotal axis for each of the leaflets is of course eccentric to the leaflet and is defined by the location of a pair of oppositely extending guides 32. The guides 32 are elongated, having a generally rectangular cross section and rounded corners to prevent chipping as the valve opens and closes. The bottom end 33 of the guide 32 has a radius of curvature that facilitates its pivotal movement.

The upstanding supports 21 each contain a pair of generally triangular-shaped depressions 41. Rear surfaces 43 of the depressions 41 in opposite supports are spaced apart so that the distance between the corresponding rear surfaces 43 is slightly longer than the distance between the vertical outer edges 44 of the guides 32. The spacing of the rear surfaces 43 of the depressions 41 allows sufficient clearance so the vertical edges 44 of the guides 32 can move freely therein, but the clearance is sufficiently small so that the rear surfaces 43 guide the vertical edges 44 allowing minimal horizontal movement of the leaflets 15. The material from which the valve body 13 is made has sufficient resiliency to allow the leaflet 15 to be snapped into position with the guides 32 being received in the depressions 41.

The periphery of each depression 41 consists of an upper curved edge 45 bridging an outer straight edge 46 and an inner straight edge 47. The straight edges 46 and 47 converge to a rounded vertex 48 which is formed with a radius of curvature matched to that of the bottom end 33 of the guides 32 to provide an extremely smooth pivot point. To allow for freedom of movement, the radius of curvature of the vertex 48 may be slightly longer, but not more than about 3% longer, than the radius of curvature of the bottom end 33. The curved upper edge 45 is spaced a suitable distance from the vertex 48 to provide a guide for the top end 49 of the guide 32 while allowing sufficient clearance for the guide 32 to freely pivot between the outer and inner edges, 46 and 47, of the depression 41.

The inner straight edge 47 may serve as a stop for the leaflet in the closed position, however, a stop is preferably provided along the edge of the leaflet itself. The outer straight edge 46 serves as a stop for the leaflet in the open position. The outer edge 46 of the depression 41 forms an angle B of between about 5° and 10° (FIG. 2) with a line parallel to the axis of the body 13, and the leaflets are thus stopped in an open position at an angle offset from the axis of the passageway so that back pressure will exert a force vector on the leaflets 15 to close the valve 11.

The inner edge 47 of the depression 41 forms an angle A (FIG. 3) with a line parallel to the axis of the passageway of between 60° and 80° to allow angular movement of the leaflets 15 of between 55° and 70°. One example of a heart valve 11 designed for aortic location may have an outer diameter of about 24 millimeters and a central passageway 17 of about 22 millimeters in diameter. The distance between the vertical edges 44 of the guides 32 may be about 1½ mm. greater than the length of the minor edge 29 of the leaflets 15.

In the open position, as depicted in FIG. 2, the main portion of the leaflet 15 has swung downward until the guides 32 abut against the outer edge 46 of the depression 41. During the opening movement, blood flows through the valve 11 in the direction of the arrow 19. This flow, of course, occurs on the pumping stroke of the heart as a respective ventricle contracts.

At the end of the stroke, the respective ventricle relaxes to draw more blood into the chamber from the atrium, and the back pressure within the left aorta causes the leaflets 15 to swing or pivot to the closed location depicted in FIG. 3. The proportioning of each leaflet 15 is such that it pivots about an axis which is defined by the radii of the curvature of the bottom ends 33 of the guides 32, until the cylindrical major edge surface 31 of the arcuate portion of each leaflet 15 contacts the interior side wall 25 of the passageway 17 thus sealing the outer regions of the passageway 17. At this point, the guides 32 will lie generally adjacent to the inner edge 47 of the depression 41, and the straight minor edge portions 29 of the leaflets 15 also preferably contact each other, closing the central portion of the passageway 17 to blood flow. There is sufficient tolerance in the region of the guides and the depressions 41 to allow sealing contact along both edges of the leaflets. Because the inner straight edge 47 is not quite reached by the guides 32 before the leaflets 15 seal the valve 11, wear is reduced in this region.

An interior face 51 of the supports 21 is flat and tangent to the cylindrical interior surface 25. A short straight segment 52 on the leaflets 15 between the guides 32 and the straight minor edge 29 of the leaflet 15 moves closely adjacent to the interior face 51 as the leaflets 15 pivot. This proportioning provides sufficient sealing between the leaflets 15 and the supports 21.

The above described embodiment provides excellent blood flow as the passageway 17 is cylindrical with no intrusions therein other than the smooth surfaced leaflets 15. The interior surfaces are all well washed by flowing blood. It is also of simple design and easily manufactured. The valve 11 with its guides pivoting in generally triangular depressions 41 provides well controlled movement of the leaflets with little friction, and the leaflets are free from sticking during use. The wear on the leaflets is so well distributed over the arcuate major edge 31 of the leaflet 15 as well as over the elongated guides 32 that it should not affect the working of the valve 11.

As previously mentioned, the flat face 51 of the support 21 is tangent to the interior surface 25 in the preferred embodiment of the valve 11 as shown in FIGS. 1–4 to allow for unobstructed blood flow. An alternative embodiment of a valve 11' is shown in FIGS. 5–7 wherein the supports 21' extend slightly across the passageway 17' so that the flat face 51' cuts a short secant over the passageway 17'. This slight overhang of the supports 21' into the passageway 17' does not significantly alter blood flow, and manufacturing considerations may suggest its use.

In the FIG. 1 embodiment described above, wear is concentrated primarily on the guides at the location where the lower end 33 of the guide 32 stops along the outer straight edge 46 of the depression 41. Shown in FIGS. 8, 9 and 10 is another embodiment of a valve 11" wherein stops are provided on supports 21". At each end of the supports 21", a stop 70 extends perpendicularly into the cylindrical passageway 17" from the otherwise flat face 51". Each stop 70 includes stopping faces 72 and 74 which contact the leaflets in the closed and open positions respectively. the face 72 stops the leaflet in the closed position at an angle of about 60° to 80° to the axis of the body 13" and the face 74 stops the leaflet in the open position at an angle of about 5° to 10° to the axis of the body 13". Because the stopping faces 72 and 74 halt the movement of the leaflets 15" in their closed and open positions, respectively, wear along the arcuate edge 31" and on the guides 32" is alleviated.

Yet another embodiment of a valve 11''' is illustrated in FIGS. 11–13 wherein closing position stops are provided as protrusions 81 on the interior wall surface 25''' of the body 13'''. At least one protrusion 81 is provided on each side of a line through the center of the supports 21''' to stop the leaflets 15''' in the closed position. The embodiment as shown in FIGS. 11–13 has two such protrusions 81 on both sides of the supports 21'''. The top of the protrusions 81 as shown is flush with the top of the cylindrical body 13''' for simplicity of machining. A beveled surface 82 on the underside of each protrusion 81 is machined so that when the valve 11''' is closed, the leaflets 15''' are flush against the beveled surface 82 and lie at an angle of between 60° and 75° relative to the axis of the central passageway 17'''. The protrusions 81 stop movement of the leaflets 15''' before the guides contact the inner edge 47''' of the depression 41''' thereby alleviating wear on the guides 32''' and on the wall of the valve depression 41'''.

Elements of the designs embodied in valves 11, 11', 11'' and 11''' may be rearranged in other combinations. For example, the flat faces 51'' and 51''' of the valves 11'' and 11''' which cut secants over the passageways 17'' and 17''' could be located tangent to the passageways, as the valve 11.

Although the invention has been described with regard to embodiments which constitute the best modes presently known in the invention, it should be understood that various changes and modifications as would be obvious to one having ordinary skill in the art may be made without departing from the scope of the invention which is defined solely by the appended claims.

What is claimed is:

1. A heart valve prosthesis comprising an annular valve body having a central passageway extending therethrough,
    a pair of valve leaflets,
    means supporting said pair of leaflets for substantially pivotal movement on a pair of eccentric axes between a closed position blocking blood flow through said central passageway and an open position allowing blood flow therethrough,
    wherein the improvement comprises,
    said leaflets each including guides projecting in opposite directions along the pivotal axis, said guides having a rounded bottom end,
    said support means including pairs of generally triangular depressions at generally diametrically opposite locations,
    each of said depressions having a curved top edge and generally straight outer and inner edges which meet at a vertex, said leaflet guides being received in said depressions with said bottom ends at the vertex thereof, said vertex being formed with a radius of curvature matched to the radius of curvature of said bottom ends and providing pivot points for each bottom end, whereby said leaflets each move between an open position wherein said guides are located generally adjacent said outer edges and a closed position wherein said guides are located generally adjacent said inner edges.

2. A prosthesis in accordance with claim 1
    wherein the valve body wall which forms said central passageway is the surface of a right circular cylinder and
    wherein the major peripheral arcuate edge of each said leaflet is contoured so that the surface of said major edge fits flush adjacent said passageway cylindrical wall.

3. A prosthesis in accordance with claim 2
    wherein a minor peripheral edge of each leaflet is straight and the edge surface thereof is planar so that the planar surfaces of said minor edges abut each other in surface-to-surface contact when said valve leaflets are in the closed position.

4. A prosthesis in accordance with claim 2 wherein the plane of each of said leaflets in the closed position makes an angle of between about 60° and about 80° with the axis of said body, and where the plane of each of said leaflets in the open position makes an angle of between about 5° and about 10° with the axis of said passageway.

5. A prosthesis in accordance with claim 1 where the radius of curvature of said vertex is equal to or not more than 3% longer than the radius of curvature of said bottom end.

6. A prosthesis in accordance with either claim 3 or claim 5 wherein each of said guides has an elongated vertical edge disposed generally perpendicular to said minor edge.

7. A prosthesis in accordance with either claim 1 or claim 3 wherein the valve body wall which forms said central passageway is the surface of a right circular cylinder and wherein at least one protrusion from said valve body wall is provided to contact each leaflet and serve as close position stop means therefor.

8. A prosthesis in accordance with claim 1 wherein upstanding supports are provided in which said said depressions are formed, said supports extending inward into said passageway and having surfaces formed thereon which stop said leaflets in the open and in the closed positions.

* * * * *